(12) United States Patent
Gleason et al.

(10) Patent No.: US 12,056,148 B2
(45) Date of Patent: *Aug. 6, 2024

(54) FEATURE SELECTION FOR ARTIFICIAL INTELLIGENCE IN HEALTHCARE MANAGEMENT

(71) Applicant: Eligible, Inc., Brooklyn, NY (US)

(72) Inventors: Katelyn Gleason, New York, NY (US); Sreehari Bellamkonda, SPSR Nellore (IN)

(73) Assignee: Eligible, Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,203

(22) Filed: Jan. 30, 2023

(65) Prior Publication Data

US 2023/0177065 A1 Jun. 8, 2023

Related U.S. Application Data

(63) Continuation of application No. 16/550,164, filed on Aug. 23, 2019, now Pat. No. 11,567,964.

(60) Provisional application No. 62/725,273, filed on Aug. 31, 2018.

(51) Int. Cl.
| | |
|---|---|
| *G06F 16/25* | (2019.01) |
| *G06F 16/245* | (2019.01) |
| *G06Q 40/08* | (2012.01) |
| *G06Q 10/063* | (2023.01) |
| *G16H 50/20* | (2018.01) |
| *G16H 50/70* | (2018.01) |
| *G16H 70/20* | (2018.01) |

(52) U.S. Cl.
CPC .......... *G06F 16/258* (2019.01); *G06F 16/245* (2019.01); *G06Q 40/08* (2013.01); *G06Q 10/063* (2013.01); *G16H 50/20* (2018.01); *G16H 50/70* (2018.01); *G16H 70/20* (2018.01)

(58) Field of Classification Search
None
See application file for complete search history.

(56) References Cited

U.S. PATENT DOCUMENTS

| | | | | |
|---|---|---|---|---|
| 2010/0324929 | A1* | 12/2010 | Petrasich | G06Q 10/00 706/46 |
| 2015/0081324 | A1* | 3/2015 | Adjaoute | G06Q 40/08 705/2 |
| 2018/0322946 | A1* | 11/2018 | Ika | G06F 21/6254 |
| 2018/0374098 | A1* | 12/2018 | Zhang | G06F 18/214 |
| 2019/0243969 | A1* | 8/2019 | Birur | G06F 21/552 |
| 2021/0118557 | A1* | 4/2021 | Pauws | G16H 40/20 |

OTHER PUBLICATIONS

Luo G. "PredicT-ML: a tool for automating machine learning model building with big clinical data;" Health Inf Sci Syst; Jun. 8, 2016; 4:5; 16 pages (Year: 2016).*

* cited by examiner

*Primary Examiner* — Rachel L. Porter
(74) *Attorney, Agent, or Firm* — Cognition IP, P.C.; Edward Steakley; Saleh Kaihani

(57) ABSTRACT

A system and method may be provided to predict a value of a field of interest about a patient procedure. Data may be received from a health provider. A statistical model or machine learning model may be built based on the data in order to predict the value of the field of interest. In some embodiments, a plurality of models are used to predict different aspects of the procedure and are combined by a main model.

20 Claims, 8 Drawing Sheets

FEATURE SELECTION FOR ARTIFICIAL INTELLIGENCE IN HEALTHCARE MANAGEMENT

CROSS-REFERENCE TO RELATED APPLICATIONS

This application is a continuation of U.S. Non-Provisional application Ser. No. 16/550,164, filed on Aug. 23, 2019, which claims the benefit of U.S. Provisional Application No. 62/725,273, filed on Aug. 31, 2018, which is hereby incorporated by reference in its entirety.

FIELD OF THE INVENTION

The present disclosure relates generally to selecting and using features to increase the accuracy of an artificial intelligence system.

BACKGROUND

Artificial intelligence (AI) relates to the use of machines to perform tasks that previously were thought to require human intelligence. AI may be applicable in some fields where large amounts of data exits. The health field, with many providers and payers, often includes significant amounts of quantitative data collected from patient visits. However, to date, the use of AI in the health field has yet to take full advantage of the many potential possibilities.

SUMMARY

In some embodiments, data is collected from a provider in order to build a statistical or machine learning model to predict one or more fields of interest from health information.

In one embodiment, data is received from a provider comprising information about a plurality of patient procedures. The data may optionally be analyzed to determine whether a statistical model can be built achieving a threshold level of accuracy. When it is determined that a statistical model can be built to achieve the threshold level of accuracy, a plurality of statistical models may be built where each model may include, for example, a selector and a plurality of sub-models that are selected on the basis of the selector. The sub-models may perform prediction based on one or more features of a query procedure. The main model may combine the outputs of the plurality of statistical models, and the main model may output a prediction of a value of a field of interest.

BRIEF DESCRIPTION OF THE DRAWINGS

The present disclosure will become better understood from the detailed description and the drawings, wherein.

DETAILED DESCRIPTION

Figure 1:
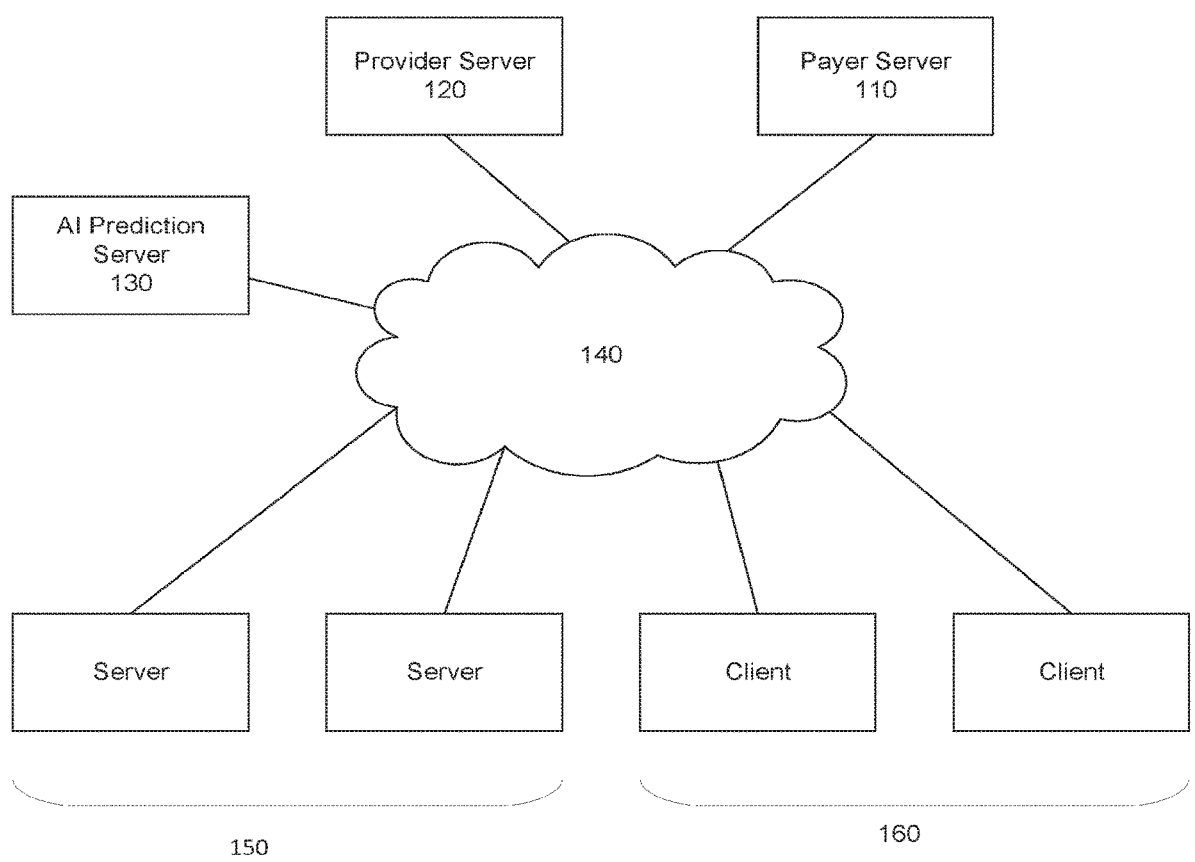
FIG. 1 illustrates a block diagram of an exemplary network environment that may be used in some embodiments.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

FIG. 1 is a block diagram illustrating an exemplary network environment that may be used in an embodiment. The network environment may include one or more clients and servers connected via a network 140. The network 140 may include a local area network (LAN), a wide area network (WAN), a telephone network, such as the Public Switched Telephone Network (PSTN), an intranet, the Internet, or a combination of networks. A payer server 110, a provider server 120, and a backend server for AI prediction 130 may be connected via the network 140. Additional servers 150 and clients 160 may also be present on the network 140. It should be understood that where the terms server or computer system are used, this includes the use of networked arrangements of multiple devices operating as a server or computer system. For example, distributed or parallel computing may be used.

A provider may be a provider of a health service, procedure, or product. For example, providers include, but are not limited to, doctors, therapists, nurses, health practitioners, hospitals, private medical practices, lab testing companies, medical device companies, and all other providers. A payer may be a payer of health insurance fees, such as an insurance company, Medicare, Medicaid, a patient, a third party, and so on. A patient may be an individual in need of or pursuing medical or health-related treatment.

Figure 2:
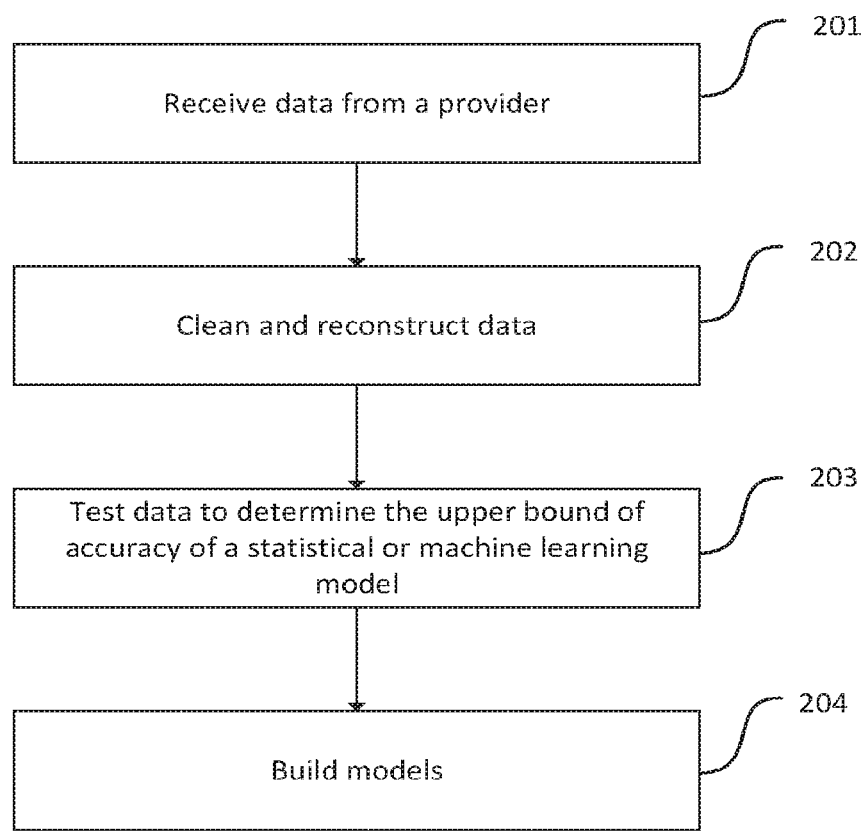
FIG. 2 illustrates an exemplary method for selecting and using features for AI prediction in health services.

FIG. 2 illustrates an exemplary method 200 for selecting and using features for AI prediction in health services. In step 201, data is received from a provider. The data received may include transaction data about patient visits and encounters, including charges by the provider, the payment by the payer, adjustments, 835 information, and other information. In step 202, the data may be cleaned and reconstructed. The data may be cleaned by identifying and removing erroneous values and also reformatting the data into a standard format. The data may also be restructured by transmitting one or more requests to servers of the payer, such as by API calls, to obtain additional information from the payer, such as health plan or benefit information. The received information may be used to be fill gaps in the data. In step 203, the data may be tested to determine the upper bound of accuracy of a statistical or machine learning model. If the upper bound is above a performance threshold, then the process of building a model may continue, and if the upper bound is below a threshold, then the process may stop. In step 204, a set of models including a price model 501, network model 502, pre-authorization model 503, risk assessment model 504, and provider model 505 are built. These models are combined by a main model 506 that accepts as input the resulting predictions of models 501-505 and outputs a final predicted price of a procedure or service and a prediction of whether the payer will accept or deny the claim. The main model 506 may be a deterministic algorithm using hard-coded rules to algebraically combined the results of the models 501-505.

In some embodiments, each model 501-505 uses a selector, where the selector comprises a set of features. Transactions that have the same values for each feature of the selector may be grouped into a sub-model. In some embodiments, each sub-model may use a different method of predicting the output. For example, the sub-models may perform prediction based on different input features.

Figure 3:
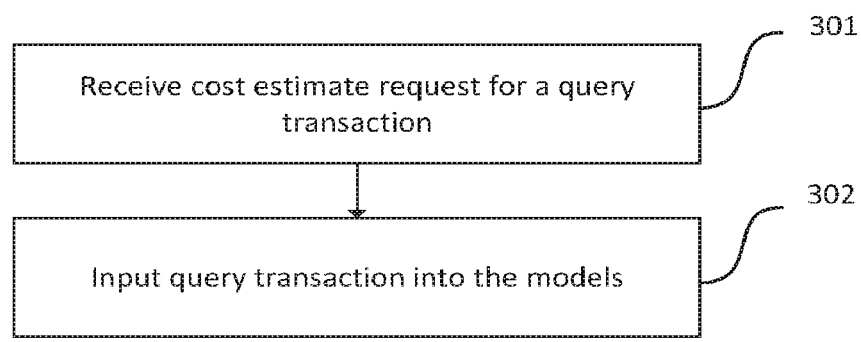
FIG. 3 illustrates an exemplary method for performing AI prediction using health data.

FIG. 3 illustrates an exemplary method 300 for performing AI prediction using health data. In step 301, cost estimate request is received for a query transaction. The query transaction may include associated information such as patient data, including name, age, gender, and other demographic information; procedure information such as a standardized procedure code; insurance information such as the plan, group, and insurance company name; and other information. In step 302, the query transaction is input into the models 501-505, which produce resulting output predictions. The resulting output predictions may be combined by main model 506 that outputs a final prediction.

Figure 4A:
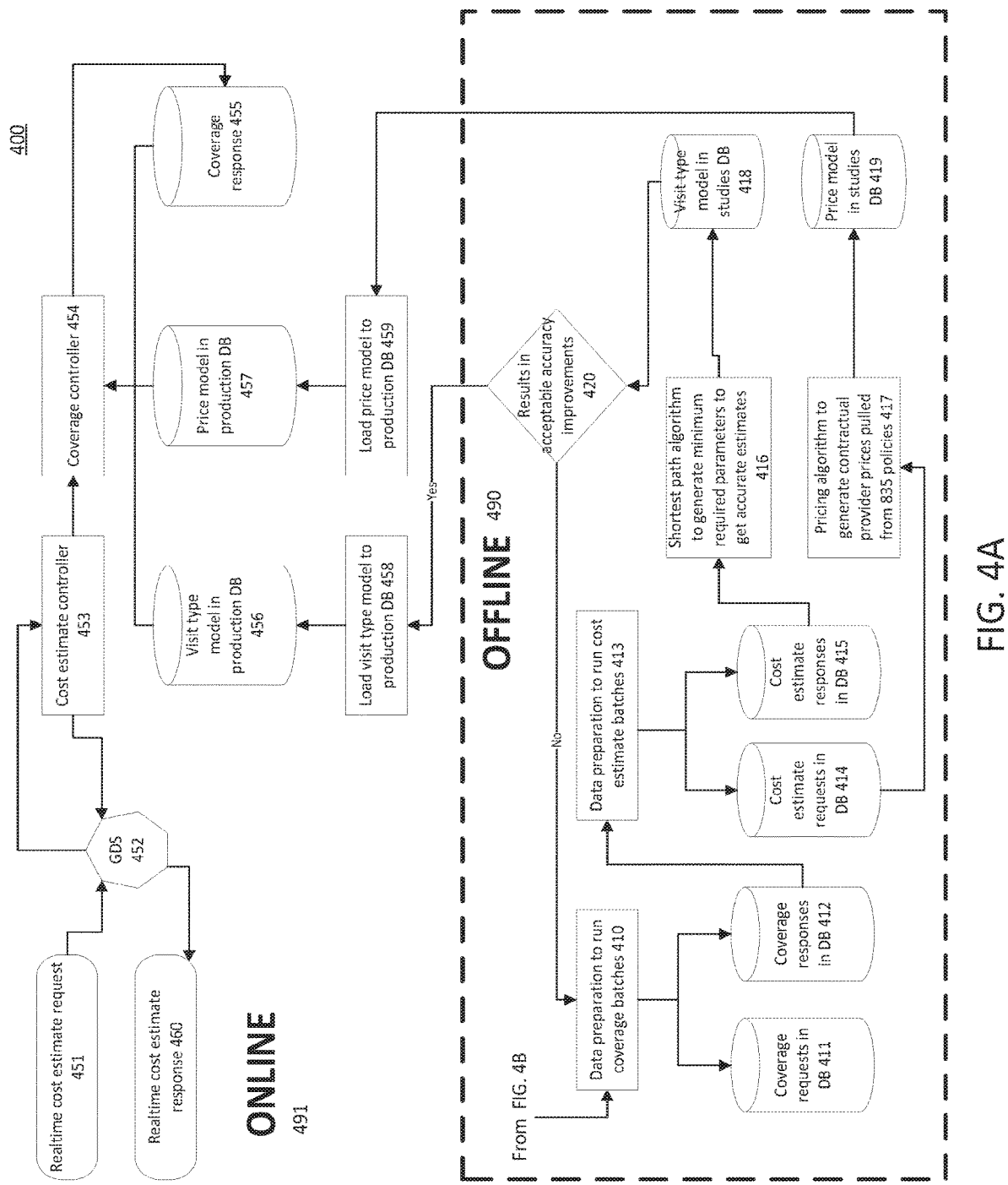
FIGS. 4A-4B illustrate an exemplary method for selecting and using features for AI prediction in health services.
Figure 4B:
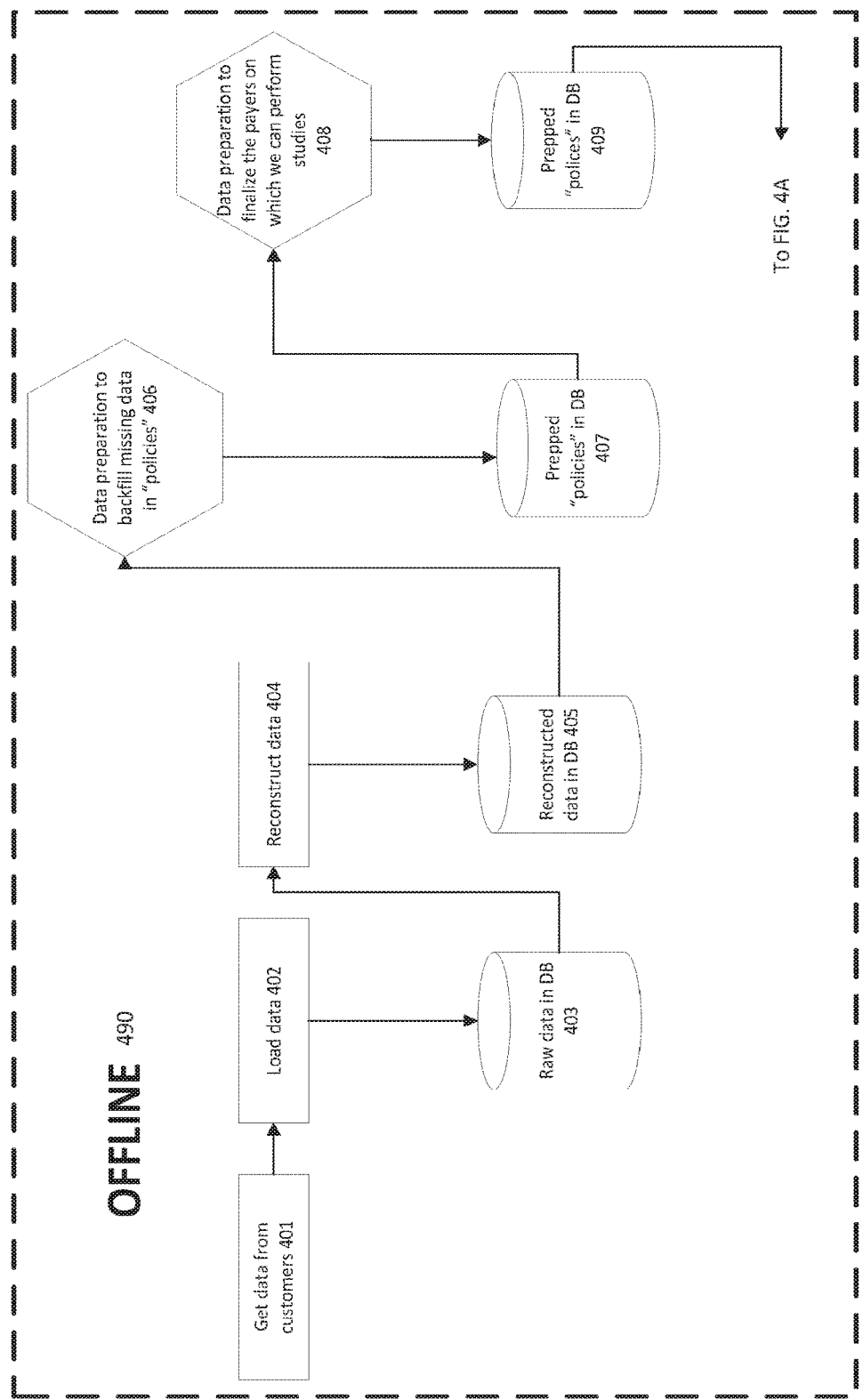

FIGS. 4A-B illustrate an exemplary method 400 for selecting and using features for AI prediction in health services. Method 400 includes an offline (490) and online (491) component that may be used separately or together. The offline component 490 is performed to build prepare the AI prediction system before usage. The online component 491 is directly responsive to user requests.

In step 401, a backend server receives data transmitted from one or more providers, labeled "customers" in the figure. The data may comprise a set of transactions including charges, payments, adjustments, and 835 information. Each transaction may comprise information such as patient information including name, address, and demographic information, date of service, and information about the service provided. Information about service provided may comprise a standardized procedure code such as a CPT code or HCPCs code. The charge may also include demographic information about the patient, the identity of the insurance company and plan, and information about the provider for the charge.

The charges may comprise information about the charge made by the provider for the transaction. Each charge may comprise an amount. The payment data may comprise information about payments made from a payer or a patient to the provider and may comprise an amount and a date. The adjustments may comprise adjustments made by the payer to the charge that was submitted by the provider. In some embodiments, adjustments are the result of contract adjustments, a discount, or a write off by the provider. The 835 information may comprise text from an 835 health care claim payment or advice. The 835 information may be text in a standardized interchange format. The 835 information may be unstructured text from the payer responding to the provider's charge.

The data received from providers may also comprise one or more fee schedules. A fee schedule may comprise schedules of common service codes, such as CPT or HCPCs codes, used by the provider and associated fees charged by the provider for those services.

In step 402, the data received from the provider is loaded into a database connected to the backend server. Herein, a database may be of any form such as table-based or non-table-based database, SQL database, NoSQL databases, and other forms of data storage. As result, raw data is stored in the database (step 403)

In step 404, the backend server reconstructs the data by accessing the raw data provided from the providers and transforming the data into a standard and common format across providers. Data from individual providers may be stored and presented in idiosyncratic and unique ways. Therefore, to use data across providers, it is important to transform the data into a common format.

The data may be structured into two types of entities, encounters and procedures. Each entity may comprise a data structure. A procedure may represent a particular procedure received by a patient on a date of service. An encounter may represent all procedures received by a patient on a date of service. Encounters and procedures may each comprise a billed amount, a contractual allowed amount, payments (from a payer, a patient, or other entity), adjustments (from a payer, patient, or other entity), and denials of payment, such as from a payer.

The reconstructed data comprising encounters and procedures is stored in Reconstructed DB 405. The Reconstructed DB 405 may also comprise additional entities known as policies. Policies may comprise charges that are suitable for us in AI prediction, which may be determined by segmenting transactions into those where the charges are settled or have a payer response. Transactions where it is determined that the charges have not settled and there is no payer response may be set aside into a secondary group that is not used for further AI prediction and may be considered to not be policies.

In step 406, data preparation is performed to backfill missing data in policies. The backend server transmits one or more requests to servers of payers to obtain more information about the policies. The requests may be transmitted by making API calls. Based on the textual payer name in the data, a payer ID such as an NPI identifier is looked up and retrieved from a database. They use the payer ID to identify and submit requests to the server of the payer and obtain financial information. The financial information may comprise information about the health plan, benefits, and insurance company information.

In some embodiments, the requests to the payer must be made including a service code to identify the service. The procedure codes from the policies may be transformed to a higher level, less descriptive identifier at the service level. In some embodiments, the service code may be at a higher level of generality than a procedure code.

In step 407, the prepped policies are in the database after the missing data has been backfilled.

In step 408, data preparation is performed to finalize the payers on which data analysis studies may be performed. One or more filters may be provided. In some embodiments, a filter comprises a determination of the identity of payers involved and whether the backend server has access to data for those payers. In some embodiments, a filter comprises a quantity of electronic calls required to a provider. In some embodiments, a filter comprises human provided instructions. Some of the payers may be filtered out and other payers may pass the filters and remain in the study. In step 409, the policies involved may be segmented according to whether the payers involved are in the study or not. Policies that are not in the study may be set aside or discarded. Policies that are in the study, based on the identity of the payer, may remain in the study.

In step 410, data preparation may be performed to run coverage batches. The backend server may make requests, such as API calls, to one or more payers to retrieve information about health plans or benefits. The retrieved information may comprise information about what procedures or services are covered and what level, type, or amount of benefits are provided for each benefit or service. It may comprise information about pricing, about providers that are in or out of network, about the necessity of pre-authorizations for some procedures or services, about medical necessity analysis, and about providers. Requests that are sent out to the payer are referred as Coverage Requests and are stored in database 411. Responses received from the payer's servers may be referred to as Coverage Responses and are stored in database 412.

In step 413, data preparation is performed to run cost estimate batches. The data may be de-identified to preserve patient privacy, such as by removing patient names and identifying information. A study is then performed on the backend server using Perfect Possible Accuracy (PPA) to see how much accuracy can be obtained using AI and statistical methods. If the PPA is determined to be above a threshold, then it is determined to proceed to try to perform prediction for this provider. If the PPA is determine do be below a threshold, then it is determined not to proceed to perform predictions for the provider.

In an embodiment, a PPA is calculated by trying segmentations on all possible combinations of features of the data to determine the accuracy in predicting a value of a field of interest. A feature may be one piece of information associated with a policy or transaction, such as the procedure, service, location, provider, patient identity, patient age, patient gender, patient demographic, in-network or out-of-network status, pre-authorization status, copayment requirement, insurance plan, insurance group, insurance company, or any other information. The transactions are segmented according to the criteria, and it is determined for each transaction whether another transaction can be found matching identical values (or having values within a specified range) for all features in the criteria and having the same value of the field of interest. If so, this is counted as a match because the AI system can potentially find a like-transaction that is a neighbor based on the features and thereby predict a correct value of the field of interest. The transactions being matched against may come from the same dataset of transactions received from the provider or may come from a previously loaded, existing dataset of transactions. The PPA may be calculated through a division step, in which the number of transactions for which a matching transaction was found comprises the numerator and the total number of transactions comprises the denominator.

After the PPA passes the threshold, steps 414, 415, 416, 417, 418, 419, 420 relate to building the model to perform prediction. In an embodiment, there are five models that perform specific functions and are combined by a main model.

Figure 5:
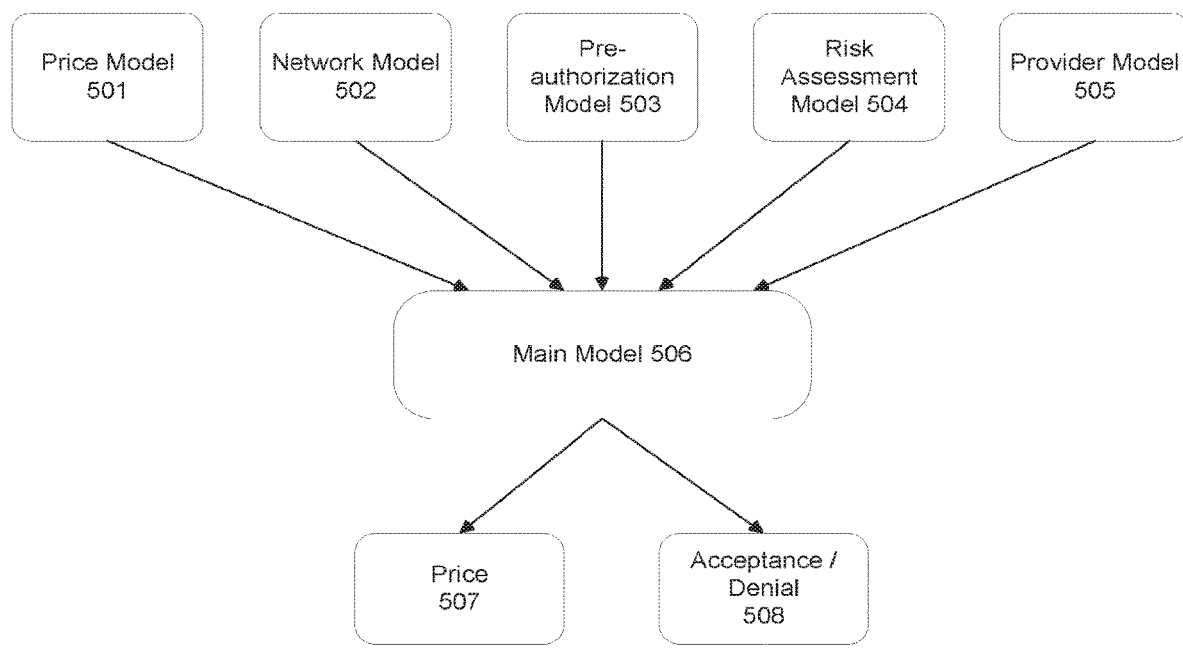
FIG. 5 illustrates exemplary models that may be used in an embodiment.

FIG. 5 illustrates models that may be used in an embodiment. First, a price model 501 is used to predict the price of a procedure or service when adjudicated by the payer. Second, a network model 502 is used to predict whether a provider will be deemed to be in-network or out-of-network. Third, a pre-authorization model 503 is used to predict whether preauthorization is required by the payer for the payer to pay the claim. Fourth, a risk assessment model 504 is used to predict whether a procedure or service will pass a medical necessity analysis, when a payer has a health plan that only pays for certain procedures or services when they are medically necessary. Fifth, a provider model 505 is used to predict what the provider identity will be when the payer adjudicates the claim. The main model 506 combines the outputs of each of these models to make a final prediction of whether the payer will accept or deny the claim 508 and the amount that the payer will pay 507.

To use the models, a transaction is input into models 501-505. The output of the models is combined in main model 506 and a result is obtained.

The PPA analysis method described above may be performed for each model 501-505 to determine whether the model will be accurate or not. If the PPA analysis fails for a model, then the backend server may determine not to build the model because the accuracy would not be sufficient. However, for each model 501-505 where the PPA is passed, a predictive model may be built.

Figure 6:
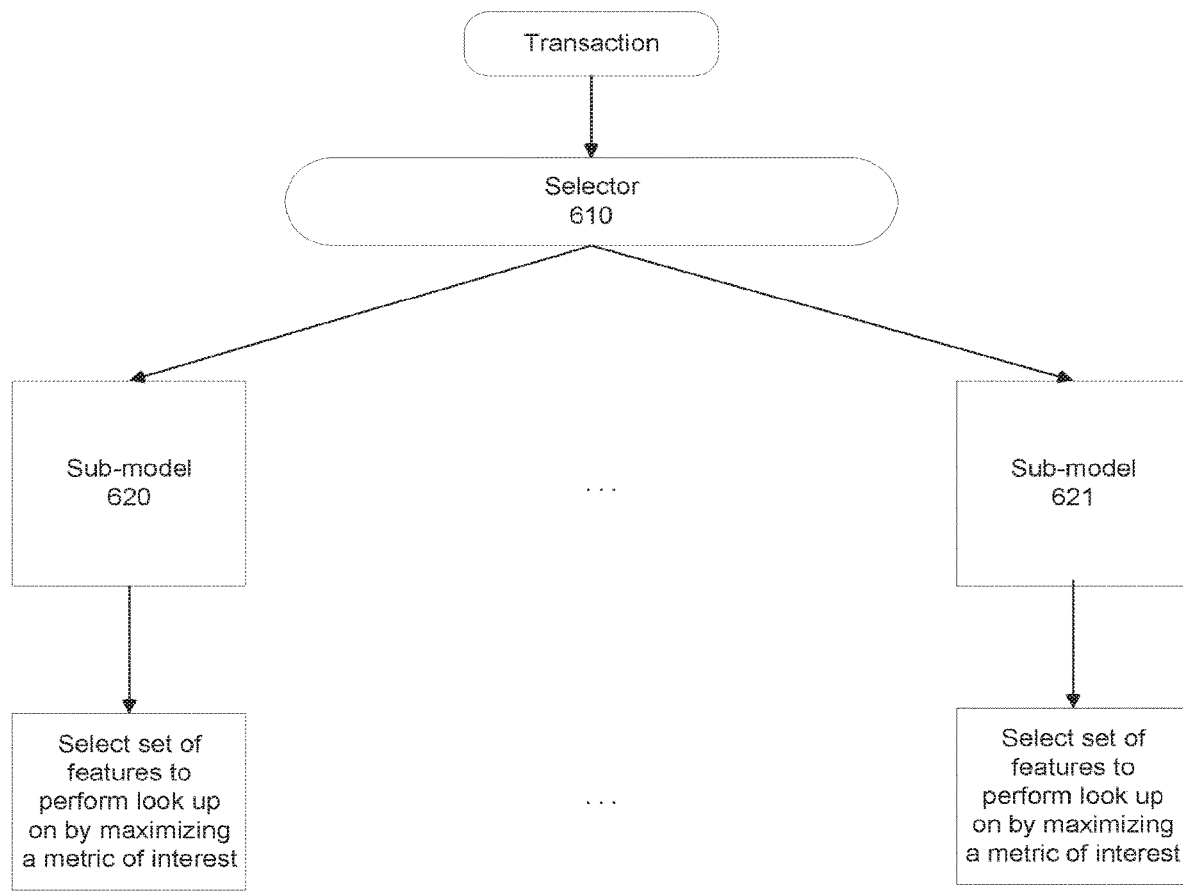
FIG. 6 illustrates an exemplary method for building models in an embodiment.

FIG. 6 illustrates a method for building models 501-505. Models 501-505 may be statistical models or machine learning models. Machine learning models may be, for example, a regression, classifier, component, module, computer program, system, or algorithm.

In an embodiment, each of the models 501-505 may be built in the following manner. In each model, each combination of values of insurance plan, insurance group, and procedure found in the dataset of transactions may be iterated over. The combination of features that is iterated over may be referred to as the selector 610. In other embodiments, other combinations of features may be used as a selector. For example, a subset of insurance plan, insurance group, and procedure may be used as a selector, or additional features may be used in the combination used as a selector.

For each of the selectors, a sub-model (such as sub-models 620, 621) may be built that is specific to the combination of values. In an embodiment, the sub-model comprises selection of a set of features that are used to look up other transactions that match on the values of those features, such as by identical match or matching within a range of values. If matching transactions are found and they all have the same value in the field of interest, then the value of the field of interest for the matching transactions is adopted as the value for the query transaction (e.g., the transaction used for the query). The field of interest may be, for example, the price for the price model, the in-network or out-of-network status for the network model, the pre-authorization requirement for the pre-authorization model, the medical necessity status for the risk assessment model, and the provider identity for the provider model. In one embodiment, if querying by the selected features leads to multiple matches with different values in the field of interest, then in one embodiment a statistical method is performed to statistically combine those values to obtain a value for the query transaction. In another embodiment, the detection of multiple matches causes the backend system to try to match on a different set of features.

In building the sub-model, all combinations of features, or a subset of them, may be iterated over and tried to determine the resulting accuracy for prediction of the value of the field of interest based on those features. The combination of features with a high accuracy, or highest accuracy, may be selected as the combination of features used for prediction in the sub-model. In some embodiments, multiple potential combinations of features are ranked based on accuracy or other quality metrics and then the desired set of features may be selected. Thus, in an embodiment, each sub-model includes a combination of features used for look up.

In another embodiment, each sub-model is a machine learning model. In this embodiment, the sub-model has a collection of transactions that have same values for the selector. The machine learning model is trained using training data that falls within the sub-model, which means that the training data has the same values for the selector features. The machine learning model is input training data having various feature values and various values of the field of interest. As a result, the machine learning model is trained to output a prediction of the field of interest based on the other features. In practice, this may be based primarily on features that are not in the selector because the features in the selector would be the same for transactions within the sub-model.

The online usage step occurs when an entity, such as a provider, payer, or patient, wants to predict the amount of cost that will be incurred for a procedure or service. In step 451 a real-time cost estimate request is received. The request may include information such as patient information including name, address, age, and demographics, information about the plan, group, and insurance company, information about the provider, and information about the procedure or service such as a standardized identifying code. Together this may comprise a query transaction, also referred to as a query encounter. The request is routed by a load balancer 452 to the cost estimate controller 453. The cost estimate controller 453 performs the cost prediction. The cost estimate controller 453 makes a request to the coverage controller 454. The coverage controller makes a request to the relevant payer's server to obtain coverage and benefit information of the patient based on their insurance information, such as the plan, group, and insurance company. Additional information that may be received include information about the plan, deductible, and benefits. Deductible information may include information about the amount of deductible and whether the deductible was met. The aforementioned information is then received from the payer's server and stored in coverage response database 455.

The cost estimate controller 453 then makes the prediction based on the information in the coverage response database 455, which may provide details of the patient's coverage, and the models 501-505. The information in the coverage response 455 may be used as variables that are plugged into the main model 506 and models 501-505 during the calculation of the resulting predicted price.

Visit type model 456 and price model 457 are illustrated here and are loaded in steps 458 and 459. It should be understood that all five models 501-505 and the main model are used in some embodiments. Moreover, additional models may also be used and combined into the main model.

During computation, each model 501-505 is used to predict each component separately. In other words, price model 501 is used to predict price, network model 502 is used to predict whether the transaction will be considered in-network or out-of-network by the payer, pre-authorization model 503 predicts whether the payer will require pre-authorization, risk assessment model 504 predicts whether the payer will consider the service or procedure to be medically necessary, and provider model 505 predicts the identity of the provider.

In an embodiment, prediction is performed in each model by identifying the features comprising the selector, then using the values of those features in the query transaction to select the corresponding sub-model. The sub-model is associated with a sub-set of features that was determined to be most predictive for the sub-model. The corresponding features appropriate for the sub-model are extracted from the query transaction and used to look up other transactions in the sub-model that have the same values for those features or values within a specified range. If all matching transactions have the same values for the field of interest, then that value is output as the prediction. If there are multiple matches that have different values in the field of interest, then a statistical method may be performed to combine the different values to determine a prediction (for example, mean, median, mode, and so on). In another embodiment, a different set of features may be tried in this situation.

In another embodiment, the sub-models are machine learning models. One or more features of the query transaction may be used by the sub-model to predict the value of the field of interest. The sub-models may be trained based on past training data from which it learns associations between fields and the value of the field of interest.

The result of the prediction from the cost estimate controller 453 may be routed back through the load balancer 452 and delivered to the requester via real-time cost estimate response 460. The cost estimate response may comprise a prediction of the price that a procedure or service will cost and whether the coverage would be accepted or denied by the payer.

Figure 7:
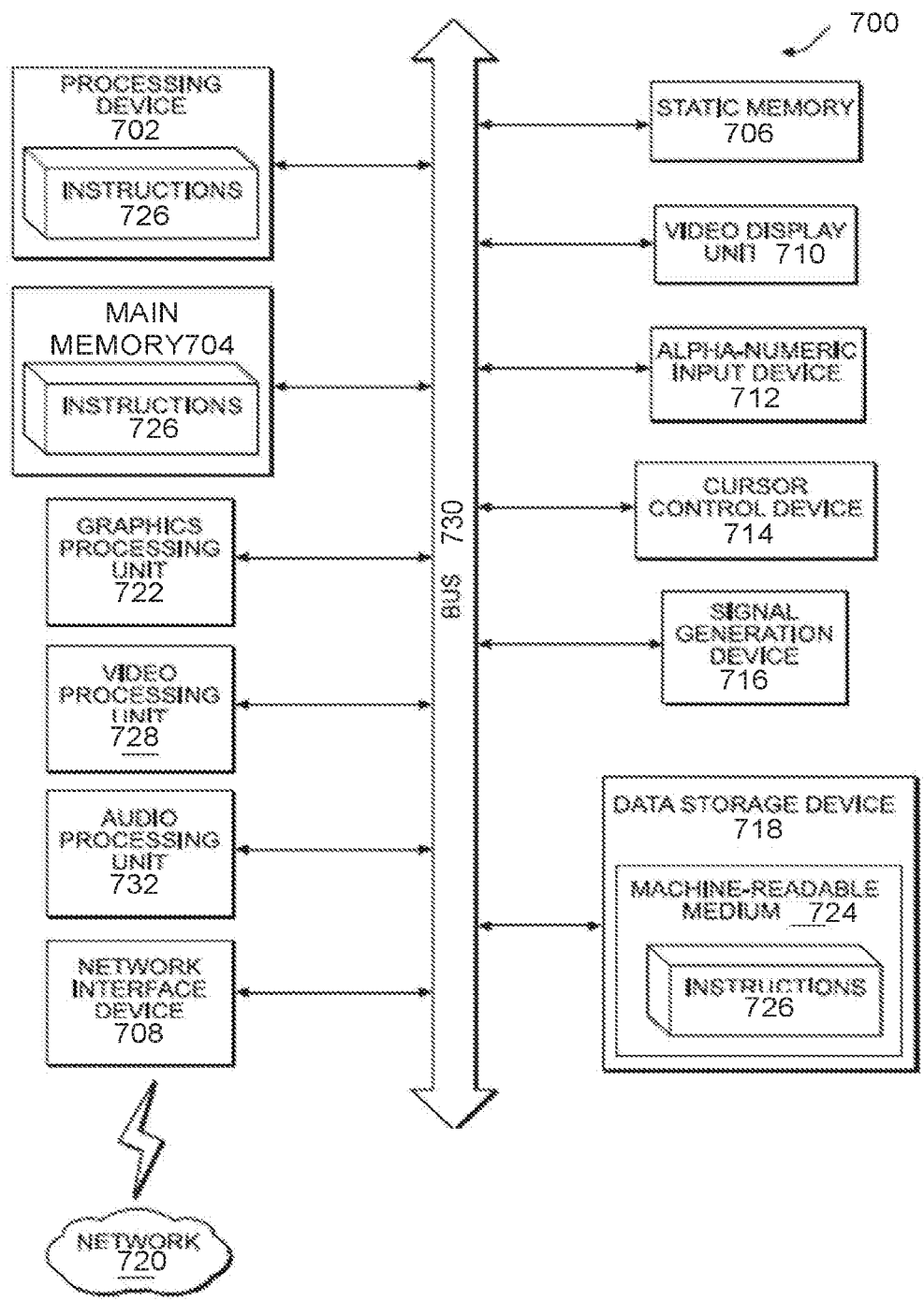
FIG. 7 illustrates an exemplary computer system that may be used in embodiments.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 715 (e.g., a mouse), a graphics processing unit 722, a signal generation device 716 (e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A method comprising:
receiving a query procedure, the query procedure comprising:
one or more query features associated with a patient and/or the patient insurance data, and
one or more request features comprising one or more of a price estimate request for an amount a payer is likely to pay for a patient procedure, a request for the likelihood of accepting or denying a claim by the payer if the price estimate amount is submitted to the payer;
receiving transaction data of a plurality of patients from a plurality of providers, the patient transaction data comprising procedures provided to the patients and cost apportionments between the patients, the providers and insurers of the patients for the provided procedures; and
building one or more machine learning models, the machine learning models comprising one or more of a price model, a network model, a pre-authorization model, a risk assessment model, a provider model, and a main model;
the machine learning models, receiving a subset of values in the transaction data and generating one or more predictions comprising one or more of a prediction of price payable by an insurer, a prediction of whether the insurer considers a procedure in network or out of network, a prediction of whether the insurer requires a pre-authorization for the procedure, a prediction of whether the insurer considers the procedure medically necessary, a prediction of identity of a provider, and a prediction of an estimated patient out of pocket cost,
wherein building each of the price model, the network model, the pre-authorization model, the risk assessment model, the provider model, and the main model comprises:
choosing a plurality of selectors, wherein each selector comprises a different combination of features in the transaction data;
for each selector,
building a machine learning sub-model based on the combination of features in the selector;
training the machine learning sub-model using training data having matching or nearly matching values for the selector features, and non-matching values for features not in the selector, wherein the trained machine learning sub-model is configured to output a prediction of a field of interest, wherein the field of interest comprises one or more features not amongst the selector features;
identifying transactions in the transaction data that share same values for the combination of features in the selector, and adopting the shared same value as output of the sub-model;
determining a prediction accuracy of a machine learning sub-model for predicting responses to the one or more request features in the query procedure, based on the adopted output;
choosing a selector yielding a high degree of prediction accuracy and adopting the machine learning sub-model of the chosen selector as the machine learning model of one or more of the price model, the network model, the pre-authorization model, the risk assessment model, or the provider model,
wherein the adopted machine learning sub-model is configured to receive the one or more query features and generate a prediction of the one or more request features,
wherein the sub-models perform prediction by identifying one or more previously settled procedures that have the same values in one or more fields as the query procedure.

2. The method of claim 1, wherein the field of interest for the price model comprises price, the field of interest for the network model comprises an in-network or out-of-network status of a procedure, the field of interest for the pre-authorization model comprises a prediction of whether an insurer requires pre-authorization for a procedure, the field of interest for the risk assessment model comprises medical necessity status for a risk assessment model, and the field of interest for the provider model comprises a provider identity.

3. The method of claim 1 further comprising:
receiving a query transaction comprising at least in part a patient data, a provider data, an insurer data, and a procedure data;
receiving patient insurance coverage data from a server of the insurer;
inputting the query transaction and the patient insurance coverage data to the trained machine learning sub-models;
receiving outputs from one or more of the trained machine learning sub-models;
based on the outputs from the trained machine learning sub-models, generating a prediction of one or more of a price, likelihood of payment by the insurer and the estimated patient out-of-pocket cost.

4. The method of claim 1, wherein the transaction data further comprises data on one or more of:
services provided by providers, fees charged by the providers, payments received by the providers, demographic information of patients receiving the services provided by the providers, identities of insurers making payments to the providers, and amounts of payments the insurers have paid the providers.

5. The method of claim 1, further comprising:
segmenting the transaction data into a first group and a second group, wherein the first group comprises transactions submitted to an insurer, with an associated response from the insurer, the second group comprises transactions submitted to an insurer without an associated response from the insurer; and
excluding the second group from the training data.

6. The method of claim 1, further comprising converting the transaction data received from the plurality of providers into a common format.

7. The method of claim 1, wherein the transaction data at least in part comprises standardized procedure codes.

8. A non-transitory computer storage that stores executable program instructions that, when executed by one or more computing devices, configure the one or more computing devices to perform operations comprising:
receiving a query procedure, the query procedure comprising:
one or more query features associated with a patient and/or the patient insurance data, and
one or more request features comprising one or more of a price estimate request for an amount a payer is likely to pay for a patient procedure, a request for the likelihood of accepting or denying a claim by the payer if the price estimate amount is submitted to the payer;

receiving transaction data of a plurality of patients from a plurality of providers, the patient transaction data comprising procedures provided to the patients and cost apportionments between the patients, the providers and insurers of the patients for the provided procedures; and building one or more machine learning models, the machine learning models comprising one or more of a price model, a network model, a pre-authorization model, a risk assessment model, a provider model, and a main model;

the machine learning models, receiving a subset of values in the transaction data and generating one or more predictions comprising one or more of a prediction of price payable by an insurer, a prediction of whether the insurer considers a procedure in network or out of network, a prediction of whether the insurer requires a pre-authorization for the procedure, a prediction of whether the insurer considers the procedure medically necessary, a prediction of identity of a provider, and a prediction of an estimated patient out of pocket cost, wherein building each of the price model, the network model, the pre-authorization model, the risk assessment model, the provider model, and the main model comprises:

choosing a plurality of selectors, wherein each selector comprises a different combination of features in the transaction data;

for each selector,
building a machine learning sub-model based on the combination of features in the selector;
training the machine learning sub-model using training data having matching or nearly matching values for the selector features, and non-matching values for features not in the selector, wherein the trained machine learning sub-model is configured to output a prediction of a field of interest, wherein the field of interest comprises one or more features not amongst the selector features
identifying transactions in the transaction data that share same values for the combination of features in the selector, and adopting the shared same value as output of the sub-model;
determining a prediction accuracy of a machine learning sub-model for predicting responses to the one or more request features in the query procedure, based on the adopted output choosing a selector yielding a high degree of prediction accuracy and adopting the machine learning sub-model of the chosen selector as the machine learning model of one or more of the price model, the network model, the pre-authorization model, the risk assessment model, or the provider model, wherein the adopted machine learning sub-model is configured to receive the one or more query features and generate a prediction of the one or more request features, wherein the sub-models perform prediction by identifying one or more previously settled procedures that have the same values in one or more fields as the query procedure.

9. The non-transitory computer storage of claim 8, wherein the field of interest for the price model comprises price, the field of interest for the network model comprises an in-network or out-of-network status of a procedure, the field of interest for the pre-authorization model comprises a prediction of whether an insurer requires pre-authorization for a procedure, the field of interest for the risk assessment model comprises medical necessity status for a risk assessment model, and the field of interest for the provider model comprises a provider identity.

10. The non-transitory computer storage of claim 8, wherein the operations further comprise:
receiving a query transaction comprising at least in part a patient data, a provider data, an insurer data, and a procedure data;
receiving patient insurance coverage data from a server of the insurer;
inputting the query transaction and the patient insurance coverage data to the trained machine learning sub-models;
receiving outputs from one or more of the trained machine learning sub-models;
based on the outputs from the trained machine learning sub-models, generating a prediction of one or more of a price, likelihood of payment by the insurer and the estimated patient out-of-pocket cost.

11. The non-transitory computer storage of claim 8, wherein the transaction data further comprises data on one or more of:
services provided by providers, fees charged by the providers, payments received by the providers, demographic information of patients receiving the services provided by the providers, identities of insurers making payments to the providers, and amounts of payments the insurers have paid the providers.

12. The non-transitory computer storage of claim 8, wherein the operations further comprise:
segmenting the transaction data into a first group and a second group, wherein the first group comprises transactions submitted to an insurer, with an associated response from the insurer, the second group comprises transactions submitted to an insurer without an associated response from the insurer; and
excluding the second group from the training data.

13. The non-transitory computer storage of claim 8, wherein the operations further comprise converting the transaction data received from the plurality of providers into a common format.

14. The non-transitory computer storage of claim 8, wherein the transaction data at least in part comprises standardized procedure codes.

15. A system comprising a processor, the processor configured to perform operations comprising:
receiving a query procedure, the query procedure comprising:
one or more query features associated with a patient and/or the patient insurance data, and
one or more request features comprising one or more of a price estimate request for an amount a payer is likely to pay for a patient procedure, a request for the likelihood of accepting or denying a claim by the payer if the price estimate amount is submitted to the payer;
receiving transaction data of a plurality of patients from a plurality of providers, the patient transaction data comprising procedures provided to the patients and cost apportionments between the patients, the providers and insurers of the patients for the provided procedures; and
building one or more machine learning models, the machine learning models comprising one or more of a price model, a network model, a pre-authorization model, a risk assessment model, a provider model, and a main model;
the machine learning models, receiving a subset of values in the transaction data and generating one or more predictions comprising one or more of a prediction of price payable by an insurer, a prediction of whether the insurer considers a procedure in network or out of network, a prediction of whether the insurer requires a pre-authorization for the procedure, a prediction of whether the insurer considers the procedure medically necessary, a prediction of identity of a provider, and a prediction of an estimated patient out of pocket cost, wherein building each of the price model, the network model, the pre-authorization model, the risk assessment model, the provider model and the main model comprises:

choosing a plurality of selectors, wherein each selector comprises a different combination of features in the transaction data;

for each selector, building a machine learning sub-model based on the combination of features in the selector;

training the machine learning sub-model using training data having matching or nearly matching values for the selector features, and non-matching values for features not in the selector, wherein the trained machine learning sub-model is configured to output a prediction of a field of interest, wherein the field of interest comprises one or more features not amongst the selector features identifying transactions in the transaction data that share same values for the combination of features in the selector, and adopting the shared same value as output of the sub-model;

determining a prediction accuracy of a machine learning sub-model for predicting responses to the one or more request features in the query procedure, based on the adopted output choosing a selector yielding a high degree of prediction accuracy and adopting the machine learning sub-model of the chosen selector as the machine learning model of one or more of the price model, the network model, the pre-authorization model, the risk assessment model, or the provider model, wherein the adopted machine learning sub-model is configured to receive the one or more query features and generate a prediction of the one or more request features, wherein the sub-models perform prediction by identifying one or more previously settled procedures that have the same values in one or more fields as the query procedure.

16. The system of claim 15, wherein the field of interest for the price model comprises price, the field of interest for the network model comprises an in-network or out-of-network status of a procedure, the field of interest for the pre-authorization model comprises a prediction of whether an insurer requires pre-authorization for a procedure, the field of interest for the risk assessment model comprises medical necessity status for a risk assessment model, and the field of interest for the provider model comprises a provider identity.

17. The system of claim 15, wherein the operations further comprise:

receiving a query transaction comprising at least in part a patient data, a provider data, an insurer data, and a procedure data;

receiving patient insurance coverage data from a server of the insurer;

inputting the query transaction and the patient insurance coverage data to the trained machine learning sub-models;

receiving outputs from one or more of the trained machine learning sub-models;

based on the outputs from the trained machine learning sub-models, generating a prediction of one or more of a price, likelihood of payment by the insurer and the estimated patient out-of-pocket cost.

18. The system of claim 15, wherein the transaction data further comprises data on one or more of:

services provided by providers, fees charged by the providers, payments received by the providers, demographic information of patients receiving the services provided by the providers, identities of insurers making payments to the providers, and amounts of payments the insurers have paid the providers.

19. The system of claim 15, wherein the operations further comprise:

segmenting the transaction data into a first group and a second group, wherein the first group comprises transactions submitted to an insurer, with an associated response from the insurer, the second group comprises transactions submitted to an insurer without an associated response from the insurer; and excluding the second group from the training data.

20. The system of claim 15, wherein the operations further comprise converting the transaction data received from the plurality of providers into a common format.

\* \* \* \* \*